United States Patent [19]

Curtis et al.

[11] Patent Number: 5,700,802
[45] Date of Patent: Dec. 23, 1997

[54] FUROPYRIDINE DERIVATIVES

[75] Inventors: Neil Roy Curtis, Puckeridge; Janusz Jozef Kulagowski, Bishops Stortford, both of England; Paul David Leeson, Monmouth Junction, N.J.

[73] Assignee: Merck Sharp & Dohme, Ltd., Hoddesdon, England

[21] Appl. No.: 727,897

[22] Filed: Oct. 9, 1996

[30] Foreign Application Priority Data

Oct. 10, 1995 [GB] United Kingdom ............... 9520731

[51] Int. Cl.$^6$ ................ A61K 31/495; C07D 405/14
[52] U.S. Cl. ............... 514/253; 514/301; 544/362; 546/115; 546/116
[58] Field of Search ............... 546/115, 116; 544/362; 514/253, 301

[56] References Cited

U.S. PATENT DOCUMENTS 5,563,152  10/1996  Kulagowski et al. ............... 546/113

OTHER PUBLICATIONS

Morita, J. Heterocyclic Chem., (1986), 23, 1465 "Furopyridines ...".

Primary Examiner—Bernard Dentz
Attorney, Agent, or Firm—Robert J. North; Melvin Winokur

[57] ABSTRACT

A class of substituted furo[2,3-b]pyridine derivatives are ligands for dopamine receptor subtypes within the body, in particular the $D_4$ subtype, and are therefore useful in the treatment and/or prevention of disorders of the dopamine system, in particular schizophrenia or depression.

13 Claims, No Drawings

FUROPYRIDINE DERIVATIVES

This invention relates to a particular class of heteroaromatic compounds. More particularly, the invention is concerned with certain substituted furo[2,3-b]pyridine derivatives. These compounds are ligands for dopamine receptor subtypes within the body, in particular the dopamine $D_4$ receptor subtype. They are therefore of use in the treatment and/or prevention of disorders of the dopamine system, including schizophrenia, depression, anxiety, nausea, Parkinson's disease, tardive dyskinesias and extrapyramidal side-effects associated with treatment by conventional neuroleptic agents, neuroleptic malignant syndrome, disorders of hypothalamic-pituitary function such as hyperprolactinaemia and amenorrhoea, and delusional disorders (cf. Catalano et al., Biol. Psychiatry, 1993, 34, 459).

Upper gastrointestinal tract motility is believed to be under the control of the dopamine system. The compounds according to the present invention may thus be of use in the prevention and/or treatment of gastrointestinal disorders, and the facilitation of gastric emptying.

Dependence-inducing agents such as cocaine and amphetamine have been shown to interact with the dopamine system. Compounds capable of counteracting this effect, including the compounds in accordance with the present invention, may accordingly be of value in the prevention or reduction of dependence on a dependence-inducing agent.

Dopamine is known to be a peripheral vasodilator; for example, it has been shown to exert a dilatory effect on the renal vascular bed. This implies that the compounds of the present invention may be beneficial in controlling vascular blood flow.

The localisation of dopamine receptor mRNA in rat heart and large vessels has been noted. This suggests a role for dopamine receptor ligands in controlling cardiovascular function, either by affecting cardiac and smooth muscle contractility or by modulating the secretion of vasoactive substances. The compounds according to the present invention may therefore be of assistance in the prevention and/or treatment of such conditions as hypertension and congestive heart failure.

By virtue of their activity as ligands for dopamine receptor subtypes within the body, the compounds in accordance with the present invention may also be of benefit in enhancing cognitive function, and in treating and/or preventing cognitive disorders including presenile and senile dementia (also known as Alzheimer's disease and senile dementia of the Alzheimer type respectively).

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., Nature (London), 1991, 350, 610) and $D_5$ (Sunahara et al., Nature (London), 1991, 350, 614) receptor subtypes have been described.

The compounds in accordance with the present invention, being ligands for dopamine receptor subtypes within the body, in particular the $D_4$ receptor subtype, and possessing advantageous properties in terms of enhanced metabolic stability, are accordingly of use in the treatment and/or prevention of disorders of the dopamine system, including schizophrenia and depression.

The present invention provides a compound of formula I, or a salt or prodrug thereof:

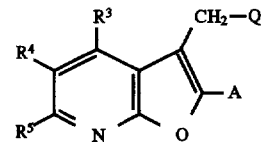

wherein

A represents hydrogen, $C_{1-6}$ alkyl, $C_{1-6}$ alkoxy, halogen, cyano or trifluoromethyl;

Q represents a moiety of formula Qa, Qb, Qc or Qd:

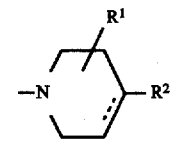

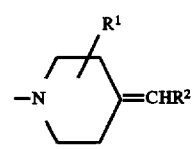

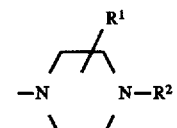

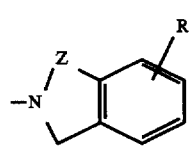

in which the broken line represents an optional chemical bond;

$R^1$ represents hydrogen, halogen, or an optionally substituted $C_{1-6}$ alkyl, $C_{1-6}$ alkoxy, $C_{2-6}$ alkenyl, $C_{2-6}$ alkynyl, aryl, aryl($C_{1-6}$)alkyl, aryl($C_{1-6}$)alkoxy, aryl ($C_{2-6}$)alkenyl, aryl($C_{2-6}$)alkynyl, $C_{3-7}$ heterocycloalkyl ($C_{1-6}$)alkyl, heteroaryl, heteroaryl($C_{1-6}$)alkyl, heteroaryl($C_{2-6}$)alkenyl or heteroaryl($C_{2-6}$)alkynyl group;

$R^2$ represents an optionally substituted $C_{1-6}$ alkyl, $C_{1-6}$ alkoxy, $C_{2-6}$ alkenyl, $C_{2-6}$ alkynyl, aryl, aryl($C_{1-6}$)alkyl, aryloxy($C_{1-6}$)alkyl, aryl($C_{1-6}$)alkoxy, aryl($C_{2-6}$) alkenyl, aryl($C_{2-6}$)alkynyl, $C_{3-7}$ heterocycloalkyl($C_{1-6}$) alkyl, heteroaryl, heteroaryl($C_{1-6}$)alkyl, heteroaryl($C_{2-6}$)alkenyl or heteroaryl($C_{2-6}$)alkynyl group;

$R^3$, $R^4$ and $R^5$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^a$ $R^b$, —$NR^aCOR^b$, —$NR^aCO_2R^b$, —$COR^a$, —$CO_2R^a$ or —$CONR^aR^b$;

Z represents —$CH_2$— or —$CH_2CH_2$—;

$R^6$ represents hydrogen or halogen, or an optionally substituted $C_{1-6}$ alkyl, $C_{1-6}$ alkoxy, aryl, aryloxy, aryl ($C_{1-6}$)alkyl, aryl($C_{1-6}$)alkoxy or heteroaryl group; and $R^a$ and $R^b$ independently represent hydrogen, hydrocarbon or a heterocyclic group.

In order to elicit their advantageous properties, the compounds according to the present invention ideally have a human dopamine $D_4$ receptor subtype binding affinity ($K_i$) of 10 nM or less, preferably 3 nM or less; and at least a 50-fold, suitably at least a 70-fold, preferably at least a 100-fold, more preferably at least a 250-fold, and most preferably at least a 500-fold, selective affinity for the $D_4$ subtype relative to the $D_2$ subtype.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds according to this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds according to the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl and aryl($C_{2-6}$)alkynyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl, heteroaryl($C_{1-6}$)alkyl, heteroaryl($C_{2-6}$)alkenyl and heteroaryl($C_{2-6}$)alkynyl groups.

Suitable alkyl groups within the scope of the term "hydrocarbon" and within the definition of the substituents A, $R^1$, $R^2$ and $R^6$ include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl and tert-butyl.

Suitable alkenyl groups within the scope of the term "hydrocarbon" and within the definition of the substituents $R^1$ and $R^2$ include straight-chained and branched alkenyl groups containing from 2 to 6 carbon atoms. Typical examples include vinyl and allyl groups.

Suitable alkynyl groups within the scope of the term "hydrocarbon" and within the definition of the substituents $R^1$ and $R^2$ include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Particular aryl groups within the scope of the term "hydrocarbon" and within the definition of the substituents $R^1$, $R^2$ and $R^6$ include phenyl and naphthyl.

Particular aryl($C_{1-6}$)alkyl groups within the scope of the term "hydrocarbon" and within the definition of the substituents $R^1$, $R^2$ and $R^6$ include benzyl, naphthylmethyl, phenethyl and phenylpropyl.

A particular aryl($C_{2-6}$)alkenyl group within the scope of the term "hydrocarbon" and within the definition of the substituents $R^1$ and $R^2$ is phenylethenyl.

Suitable heterocycloalkyl groups include azetidinyl, pyrrolidinyl, piperidinyl, piperazinyl, morpholinyl and tetrahydrofuryl groups.

A particular $C_{3-7}$ heterocycloalkyl($C_{1-6}$)alkyl group within the scope of the expression "a heterocyclic group" and within the definition of the substituents $R^1$ and $R^2$ is tetrahydrofurylethyl.

Suitable heteroaryl groups within the scope of the expression "a heterocyclic group" and within the definition of the substituents $R^1$, $R^2$ and $R^6$ include pyridinyl, quinolinyl, isoquinolinyl, pyridazinyl, pyrimidinyl, pyrazinyl, pyranyl, furyl, benzofuryl, dibenzofuryl, thienyl, benzthienyl, indolyl, indazolyl, imidazolyl, benzimidazolyl, oxadiazolyl and thiadiazolyl groups.

Particular heteroaryl($C_{1-6}$)alkyl groups within the scope of the expression "a heterocyclic group" and within the definition of the substituents $R^1$ and $R^2$ include thienylmethyl, pyridinylmethyl, pyrimidinylmethyl and pyrazinylmethyl.

The hydrocarbon and heterocyclic groups, as well as the substituents $R^1$, $R^2$ and $R^6$, may in turn be optionally substituted by one or more groups selected from $C_{1-6}$ alkyl, adamantyl, phenyl, aryl($C_{1-6}$)alkyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, trifluoromethanesulphonyloxy, —NR'R", —NR'COR", —NR'CO$_2$R", —NR'SO$_2$R", —CH$_2$NR'SO$_2$R", —NHCONR'R", —PO(OR$^v$)(OR$^w$), —CONR'R", —SO$_2$NR'R" and —CH$_2$SO$_2$NR'R", in which R$^v$ and R$^w$ independently represent hydrogen, $C_{1-6}$ alkyl, aryl or aryl($C_{1-6}$)alkyl.

The term "halogen" as used herein includes fluorine, chlorine, bromine and iodine, especially fluorine and chlorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Suitably, the substituent A represents hydrogen or $C_{1-6}$ alkyl, particularly hydrogen or methyl, and especially hydrogen.

Suitably, the substituent $R^1$ represents hydrogen.

Typical values for the substituent $R^2$ include aryl, aryl($C_{1-6}$)alkyl, aryloxy($C_{1-6}$)alkyl, aryl($C_{2-6}$)alkenyl, aryl($C_{2-6}$)alkynyl, $C_{3-7}$ heterocycloalkyl($C_{1-6}$)alkyl, heteroaryl, heteroaryl($C_{1-6}$)alkyl and heteroaryl($C_{2-6}$)alkenyl, any of which groups may be optionally substituted. Suitably, $R^2$ is selected from aryl, aryl($C_{2-6}$)alkenyl, aryl($C_{2-6}$)alkynyl and heteroaryl, any of which groups may be optionally substituted. Examples of optional substituents on the group $R^2$ include $C_{1-6}$ alkyl, halogen, $C_{1-6}$ alkoxy, $C_{1-3}$ alkylenedioxy, nitro, cyano, aryloxy and arylcarbonyloxy.

Particular values of $R^2$ include phenyl, chlorophenyl, ethylphenyl, methoxyphenyl, nitrophenyl, naphthyl, benzyl, chlorobenzyl, phenethyl, phenoxy-methyl, phenylethenyl, fluoro-phenylethenyl, chloro-phenylethenyl, methoxy-phenylethenyl, cyano-phenylethenyl, methylenedioxy-phenylethenyl, phenylethynyl, fluoro-phenylethynyl, tetrahydrofuryl-ethyl, indolyl, benzofuryl, benzthienyl, furylethyl, methyl-furylethyl, thienylethenyl and methyl-furylethenyl.

More particularly, $R^2$ may represent phenyl, chlorophenyl, methoxyphenyl, phenylethenyl, fluoro-phenylethenyl, chloro-phenylethenyl, cyano-phenylethenyl, methylenedioxy-phenylethenyl, phenylethynyl, fluoro-phenylethynyl or benzofuryl, especially chlorophenyl or phenylethenyl.

Suitable values for the substituents $R^3$, $R^4$ and $R^5$ include hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy and $C_{2-6}$ alkylcarbonyl. Particular values include hydrogen, fluoro, chloro, methyl, methoxy and benzyloxy, typically hydrogen, fluoro or methoxy, and especially hydrogen.

Particular values of $R^6$ include hydrogen, methoxy, phenyl, chlorophenyl, phenoxy, benzyloxy, thienyl, chloro and bromo, especially hydrogen.

One sub-class of compounds according to the invention is represented by the compounds of formula IIA, and salts and prodrugs thereof:

(IIA)

wherein:

E represents —$(CH_2)_n$—, —CH=CH— or —C≡C—;
n is zero, 1, 2 or 3;

—X—Y— represents —$CH_2$—CH—, —CH=C— or —$CH_2$—N—;

W represents a group of formula (i), (ii), (iii), (iv), (v) or (vi):

(i)

(ii)

(iii)

(iv)

(v)

(vi)

in which V represents oxygen, sulphur, NH or N-methyl; and $R^{13}$ and $R^{17}$ independently represent hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$) alkoxy or $C_{2-6}$ alkylcarbonyl.

Particular values of $R^{13}$ include hydrogen, fluoro, chloro, methyl, ethyl, methoxy and benzyloxy, especially hydrogen.

Particular values of $R^{17}$ include hydrogen and halogen, especially hydrogen or chloro.

In a subset of the compounds of formula IIA, W represents a group of formula (i), in particular wherein $R^{17}$ is hydrogen or halogen, especially hydrogen or chloro.

Another sub-class of compounds according to the invention is represented by the compounds of formula IIB, and salts and prodrugs thereof:

(IIB)

wherein $R^{13}$ is as defined with reference to formula IIA above; and $R^{16}$ represents hydrogen, halogen, $C_{1-6}$ alkyl, $C_{1-6}$ alkoxy, aryl, halo-aryl, aryloxy, aryl($C_{1-6}$)alkyl, aryl($C_{1-6}$) alkoxy or heteroaryl.

Particular values of $R^{16}$ include hydrogen, methoxy, phenyl, chlorophenyl, phenoxy, benzyloxy, thienyl, chloro and bromo.

Specific compounds within the scope of the present invention include:

3-[4-(E)-(2-phenylethenyl)-1,2,3,6-tetrahydropyridin-1-yl] methylfuro[2,3-b]pyridine;

3-[4-(4-chlorophenyl)-1,2,3,6-tetrahydropyridin-1-yl] methylfuro[2,3-b]pyridine;

3-[4-(4-chlorophenyl)piperazin-1-yl]methylfuro[2,3-b] pyridine;

and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Favoured unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of schizophrenia or depression, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

In order to alleviate the symptoms of schizophrenia without causing sedation or extrapyramidal side-effects, the dosage level of the compound according to the invention is ideally selected such that the dose administered is effective in substantially completely blocking the dopamine $D_4$ receptor subtype in human brain whilst displaying no or negligible dopamine $D_2$ receptor subtype occupancy. A suitable dosage level in this regard is about 0.001 to 5.0 mg/kg per day, more particularly about 0.005 to 1.0 mg/kg per day, and especially about 0.01 to 0.5 mg/kg per day.

If desired, the compounds according to this invention may be co-administered with another medicament, for example a known anti-schizophrenic agent which produces its effects via dopamine $D_2$ and/or $5\text{-}HT_2$ receptor blockade. Such co-administration may be desirable where a patient is already established on an anti-schizophrenic treatment regime involving conventional anti-schizophrenic medicaments such as haloperidol or chlorpromazine.

The compounds in accordance with the present invention may be prepared by a process which comprises reacting a compound of formula III with a compound of formula IV:

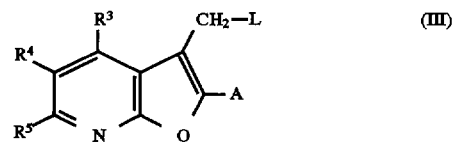

wherein A, $R^3$, $R^4$ and $R^5$ are as defined above, $Q^1$ represents the residue of a moiety of formula Qa to Qd as defined above, and L represents a suitable leaving group.

The leaving group L is suitably a halogen atom, e.g. chlorine or bromine.

The reaction is conveniently carried out by stirring the reactants under basic conditions in a suitable solvent, for example potassium carbonate in N,N-dimethylformamide, or triethylamine in tetrahydrofuran or acetonitrile.

In an alternative procedure, the compounds according to the invention may be prepared by a process which comprises reducing a compound of formula V:

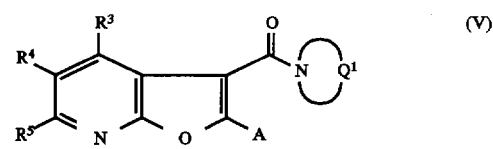

wherein A, $R^3$, $R^4$, $R^5$ and $Q^1$ are as defined above.

The reaction is conveniently carried out by treating compound V with a suitable reducing agent, typically lithium aluminium hydride, in an appropriate solvent, e.g. tetrahydrofuran.

The preparation of the intermediates of formula V is illustrated by the following reaction scheme:

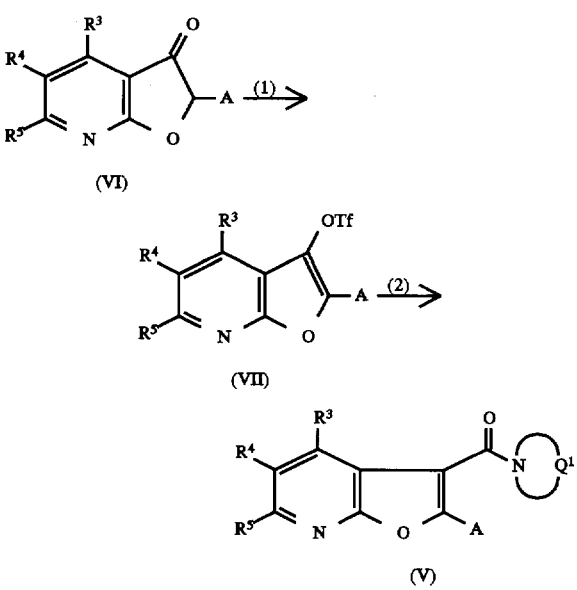

in which A, $R^3$, $R^4$, $R^5$ and $Q^1$ are as defined above; and Tf is an abbreviation for triflyl (trifluoromethanesulphonyl).

In step (1), the cyclic ketone of formula VI is reacted with triflic anhydride ($Tf_2O$), advantageously in the presence of a base such as 2,6-di-tert-butyl-4-methylpyridine, and suitably in an inert solvent such as dichloromethane. The intermediate of formula VII thereby obtained is then reacted in step (2) with carbon monoxide and the appropriate compound of formula IV as defined above, the reaction being suitably mediated by palladium(II) acetate in the presence of 1,1'-bis(diphenylphosphino)ferrocene (DPPF).

The starting compounds of formula VI above may be prepared by the method described in *J. Heterocycl. Chem.*, 1986, 23, 1465; or by procedures analogous thereto.

The compounds of formula III above wherein L is chloro may be prepared by firstly reacting the appropriate compound of formula VII as defined above with carbon monoxide and methanol, advantageously in the presence of palladium(II) acetate and DPPF. The resulting methyl ester derivative is then reduced, typically with diisobutylaluminium hydride (DIBAL), to the corresponding hydroxymethyl analogue, which in turn is reacted with thionyl chloride to give the required chloro compound.

Where they are not commercially available, the starting materials of formula IV may be prepared by procedures analogous to those described in the accompanying Examples, or by standard methods well known from the art.

It will be appreciated that any compound of formula I initially obtained from any of the above processes may, where appropriate, subsequently be elaborated into a further desired compound of formula I using techniques known from the art.

Where the above-described processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds useful in this invention potently inhibit [$^3$H]-spiperone binding to human dopamine $D_4$ receptor subtypes expressed in clonal cell lines. Moreover, the compounds according to the invention display a selective affinity for the $D_4$ subtype relative to the $D_2$ subtype.

[$^3$H]-Spiperone Binding Studies

Clonal cell lines expressing the human dopamine $D_4$ receptor subtype were harvested in PBS and then lysed in 10 mM Tris-HCl pH 7.4 buffer containing 5 mM $MgSO_4$ for 20 min on ice. Membranes were centrifuged at 50,000 g for 15 min at 4° C. and the resulting pellets resuspended in assay buffer (50 mM Tris-HCl pH 7.4 containing 5 mM EDTA, 1.5 mM $CaCl_2$, 5 mM $MgCl_2$, 5 mM KCl, 120 mM NaCl, and 0.1% ascorbic acid) at 20 mg/ml wet weight. Incubations were carried out for 60 min at room temperature (22° C.) in the presence of 0.05–2 nM [$^3$H]-spiperone or 0.2 nM for displacement studies and were initiated by addition of 20–100 μg protein in a final assay volume of 0.5 ml. The incubation was terminated by rapid filtration over GF/B filters presoaked in 0.3% PEI and washed with 10 ml ice-cold 50 mM Tris-HCl, pH 7.4. Specific binding was determined by 10 μM apomorphine and radioactivity determined by counting in a LKB beta counter. Binding parameters were determined by non-linear least squares regression analysis, from which the inhibition constant $K_i$ could be calculated for each test compound.

The compounds of the accompanying Examples were tested in the above assay, and all were found to possess a $K_i$ value for displacement of [$^3$H]-spiperone from the human dopamine $D_4$ receptor subtype of below 1.5 μM.

EXAMPLE 1

3-(4-(4-Chlorophenyl)-1,2,3,6-tetrahydropyridin-1-yl)methylfuro[2,3-b]pyridine

Step 1: Methyl furo[2,3-b]pyridine-3-carboxylate 2,6-Di-tert-butyl-4-methylpyridine (1.09 g, 5.31 mmol) was added to a solution of furo[2,3-b]pyridin-3(2H)-one (0.65 g, 4.8 mmol) [prepared by the method of H. Morita and S. Shiotani, *J. Het. Chem.*, 1986, 23, 1465] in dichloromethane (20 ml) at −5° C. Trifluoromethanesulfonic anhydride (0.89 ml, 5.29 mmol) was added slowly to the reaction mixture and the resulting solution stirred at −5° C. to 0° C. for 2.5 hours. The mixture was allowed to warm to room temperature, poured into water (100 ml) and extracted with dichloromethane (2×50 ml). The combined extracts were dried ($MgSO_4$), concentrated in vacuo and the residual oil plus solid triturated with ethyl acetate. The mixture was filtered and the filtrate evaporated to afford crude triflate, which was dissolved in dimethylformamide (10 ml). Methanol (4 ml), triethylamine (1.4 ml, 10 mmol), palladium(II) acetate (30.4 mg, 0.135 mmol), and 1,1'-bis(diphenylphosphino)ferrocene (153.7 mg, 0.277 mmol) were added, the mixture purged with carbon monoxide for 15 minutes and then stirred under a carbon monoxide balloon at 60° C. for 6 hours. The reaction mixture was allowed to cool, diluted with water (150 ml) and extracted with ethyl acetate (2×100 ml). The extracts were washed with brine (100 ml), combined and dried ($MgSO_4$). The solvent was evaporated and the residue purified by flash chromatography, eluting with 1:3 then 1:2 ethyl acetate/petrol (60°–80°), to give the title compound (0.28 g, 33%) as a pale lemon solid; $\delta_H$ ($CDCl_3$) 3.96 (3H, s, $CO_2CH_3$), 7.37 (1H, dd, J 7.5, 5.2 Hz, 5-H), 8.34 (1H, s, 2-H), 8.40 (2H, m, 4-H, 6-H).

Step 2: 3-Hydroxymethylfuro[2,3-b]pyridine

Diisobutylaluminium hydride in toluene (1.5M; 2.4 ml, 3.6 mmol) was added dropwise to a solution of methyl furo[2,3-b]pyridine-3-carboxylate (0.28 g, 1.58 mmol) in tetrahydrofuran (10 ml) at −75° C. The resulting solution was stirred at −75° C. for 40 minutes, the cooling bath removed and the mixture allowed to warm to room temperature. The reaction mixture was stirred at room temperature for 15 minutes, recooled to −40° C. and quenched by sequential addition of methanol (0.5 ml), water (0.25 ml) and 2M sodium hydroxide (0.25 ml). The mixture was allowed to warm up to produce a gel (exotherm observed), which was filtered off and washed with dichloromethane (8×10 ml). The filtrate was evaporated, the residue redissolved in dichloromethane and the solution dried (MgSO₄). The solution was concentrated in vacuo to afford the title compound (0.2182 g, 93%) as a colourless solid; δ$_H$ (CDCl₃) 1.94 (1H, br s, CH₂OH), 4.85 (2H, s, CH₂OH), 7.26 (1H, dd, J 7.6, 4.9 Hz, 5-H), 7.69 (1H, s, 2-H), 8.05 (1H, dd, J 7.6, 1.7 Hz, 4-H), 8.34 (1H, dd, J 4.9, 1.7 Hz, 6-H).

Step 3: 3-(4-(4-Chlorophenyl)-1,2,3,6-tetrahydropyridin-1-yl)methylfuro[2,3-b]pyridine 3-Hydroxymethylfuro[2,3-b]pyridine (101.5 mg, 0.681 mmol) was treated with thionyl chloride (2 ml) and the solution stirred at room temperature for an hour. The mixture was concentrated in vacuo, toluene added (5 ml) and evaporated to dryness. The residue was dissolved in anhydrous dimethylformamide (5 ml), potassium carbonate (0.47 g, 3.40 mmol) and 4-(4-chlorophenyl)-1,2,3,6-tetrahydropyridine hydrochloride (173.3 mg, 0.753 mmol) were added and the mixture stirred at room temperature, under nitrogen, overnight (19 hours). The reaction mixture was poured into water (50 ml) and extracted with ethyl acetate (2×25 ml). The extracts were washed with brine (25 ml), combined, dried (MgSO₄) and the residue after evaporation purified by flash chromatography, eluting with 1:1 then 2:1 ethyl acetate/hexane, to afford the title compound (118.3 mg, 54%) as a pale yellow solid. Recrystallisation from ethyl acetate/hexane gave yellow plates, m.p. 115.5°–116.5° C.; (Found: C, 70.06; H, 5.19; N, 8.52. C₁₉H₁₇ClN₂O requires C, 70.26; H, 5.28; N, 8.62%); δ$_H$ (CDCl₃) 2.54 (2H, br s, tetrahydropyridinyl CH₂), 2.78 (2H, t, J 5.6 Hz, tetrahydropyridinyl CH₂), 3.23 (2H, m, tetrahydropyridinyl CH₂), 3.78 (2H, s, ArCH₂N), 6.06 (1H, t, J 3.5 Hz, tetrahydropyridinyl CH), 7.21–7.32 (5H, m, ArH), 7.68 (1H, s, 2-H), 8.12 (1H, dd, J 7.6, 1.7 Hz, 4-H), 8.34 (1H, dd, J 4.8, 1.7 Hz, 6-H); m/z (ES⁺) 325/327 (M+1)⁺.

Prepared in an analogous manner were:

EXAMPLE 2

(E)-3-(4-(2-Phenylethenyl)-1,2,3,6-tetrahydropyridin-1-yl)methylfuro[2,3-b]pyridine M.p. 137.5°–138 ° C. (dec.) (ethyl acetate/hexane); (Found: C, 79.68; H, 6.36; N, 9.03. C₂₁H₂₀N₂O requires C, 79.72; H, 6.37; N, 8.85%); δ$_H$ (CDCl₃) 2.42 (2H, br s, tetrahydropyridinyl CH₂), 2.71 (2H, t, J 5.7 Hz, tetrahydropyridinyl CH₂), 3.19 (2H, m, tetrahydropyridinyl CH₂), 3.74 (2H, s, ArCH₂N), 5.82 (2H, br s, tetrahydropyridinyl CH), 6.45 (1H, d, J 16.2 Hz, CH=CHPh), 6.79 (1H, d, J 16.2 Hz, CH=CHPh), 7.18–7.24 (2H, m, ArH, 5-H), 7.30 (2H, m, ArH), 7.40 (2H, d, J 7.4 Hz, ArH), 7.65 (1H, s, 2-H), 8.11 (1H, dd, J 7.6, 1.7 Hz, 4-H), 8.33 (1H, dd, J 4.9, 1.7 Hz, 6-H); m/z (ES⁺) 317 (M+1)⁺.

EXAMPLE 3

3-(4-(4-Chlorophenyl)piperazin-1-yl)methylfuro[2,3]-pyridine

M.p. 128°–129° C. (ethyl acetate/hexane); (Found: C, 66.14; H, 5.42; N, 12.84. C₁₈H₁₈ClN₃O requires C, 65.95; H, 5.53; N, 12.82%); δ$_H$ (CDCl₃) 2.64 (4H, t, J 5.0 Hz, 2×piperazinyl CH₂), 3.16 (4H, t, J 5.0 Hz, 2×piperazinyl CH₂), 3.69 (2H, s, ArCH₂N), 6.82 (2H, m, ArH), 7.17–7.25 (3H, m, ArH), 7.64 (1H, s, 2-H), 8.11 (1H, dd, J 7.6, 1.7 Hz, 4-H), 8.34 (1H, dd, J 4.9, 1.7 Hz, 6-H); m/z (ES⁺) 328/330 (M+1)⁺.

We claim:

1. A compound of formula I, or a salt or prodrug thereof:

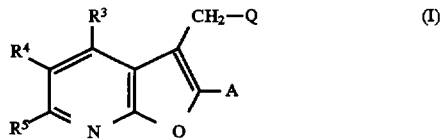

wherein

A represents hydrogen, C$_{1-6}$ alkyl, C$_{1-6}$ alkoxy, halogen, cyano or trifluoromethyl;

represents a moiety of formula Qa, Qb, Qc or Qd:

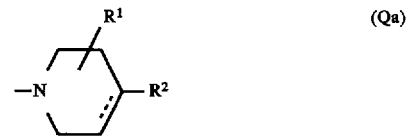

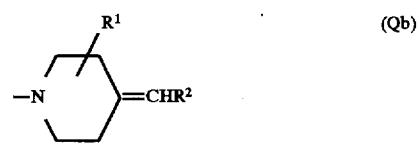

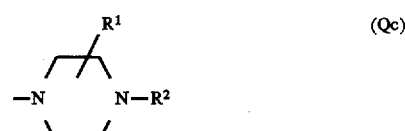

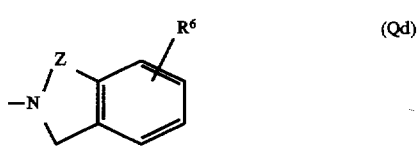

in which the broken line represents an optional chemical bond;

R$^1$ represents hydrogen, halogen, or an optionally substituted C$_{1-6}$ alkyl, C$_{1-6}$ alkoxy, C$_{2-6}$ alkenyl, C$_{2-6}$ alkynyl, aryl, aryl(C$_{1-6}$)alkyl, aryl(C$_{1-6}$)alkoxy, aryl(C$_{2-6}$)alkenyl, aryl(C$_{2-6}$)alkynyl, C$_{3-7}$ heterocycloalkyl (C$_{1-6}$)alkyl, heteroaryl, heteroaryl(C$_{1-6}$)alkyl, heteroaryl(C$_{2-6}$)alkenyl or heteroaryl(C$_{2-6}$)alkynyl group;

R$^2$ represents an optionally substituted C$_{1-6}$ alkyl, C$_{1-6}$ alkoxy, C$_{2-6}$ alkenyl, C$_{2-6}$ alkynyl, aryl, aryl(C$_{1-6}$)alkyl, aryloxy(C$_{1-6}$)alkyl, aryl(C$_{1-6}$)alkoxy, aryl(C$_{2-6}$) alkenyl, aryl(C$_{2-6}$)alkynyl, C$_{3-7}$ heterocycloalkyl(C$_{1-6}$) alkyl, heteroaryl, heteroaryl(C$_{1-6}$)alkyl, heteroaryl(C$_{2-6}$)alkenyl or heteroaryl(C$_{2-6}$)alkynyl group;

R$^3$, R$^4$ and R$^5$ independently represent hydrogen, hydrocarbon, a heterocyclic group, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$ or —CONR$^a$R$^b$;

Z represents —CH$_2$— or —CH$_2$CH$_2$—;

R$^6$ represents hydrogen or halogen, or an optionally substituted C$_{1-6}$ alkyl, C$_{1-6}$ alkoxy, aryl, aryloxy, aryl (C$_{1-6}$)alkyl, aryl(C$_{1-6}$)alkoxy or heteroaryl group; and R$^a$ and R$^b$ independently represent hydrogen, hydrocarbon or a heterocyclic group.

2. A compound as claimed in claim 1 wherein A represents hydrogen.

3. A compound as claimed in claim 1 wherein Q represents a moiety of formula Qa or Qc.

4. A compound as claimed in claim 1 wherein $R^1$ represents hydrogen.

5. A compound as claimed in claim 1 wherein $R^2$ represents chlorophenyl or phenylethenyl.

6. A compound as claimed in claim 1 wherein $R^3$, $R^4$ and $R^5$ each represents hydrogen.

7. A compound as claimed in claim 1 represented by formula IIA, and salts and prodrugs thereof:

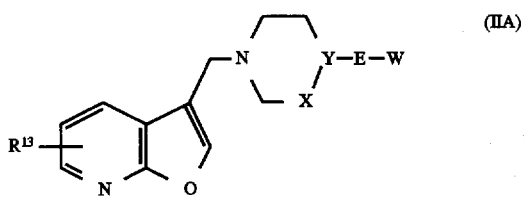

wherein

E represents —$(CH_2)_n$—, —CH=CH— or —C≡C—;

n is zero, 1, 2 or 3;

—X—Y— represents —$CH_2$—CH—, —CH=C— or —$CH_2$—N—;

W represents a group of formula (i), (ii), (iii), (iv), (v) or (vi):

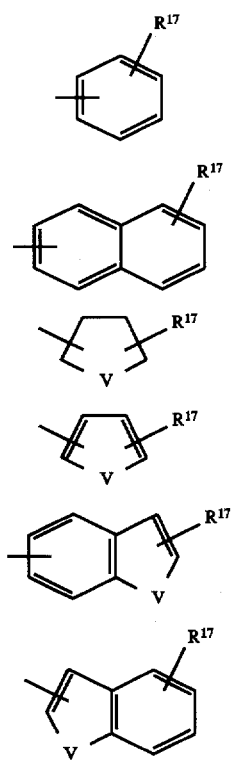

in which V represents oxygen, sulphur, NH or N-methyl; and $R^{13}$ and $R^{17}$ independently represent hydrogen, halogen, cyano, nitro, trifluoromethyl, amine, $C_{1-6}$ alkylamino, di($C_{1-6}$)alkylamino, $C_{1-6}$ alkyl, $C_{1-6}$ alkoxy, aryl($C_{1-6}$) alkoxy or $C_{2-6}$ alkylcarbonyl, with the proviso that when n is zero, then W does not represent a group of formula (iii) as defined above.

8. A compound as claimed in claim 7 wherein $R^{13}$ represents hydrogen.

9. A compound as claimed in claim 7 wherein $R^{17}$ represents hydrogen or chloro.

10. A compound as claimed in claim 1 represented by formula IIB, and salts and prodrugs thereof:

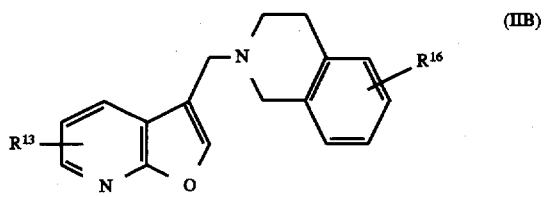

$R^{13}$ is hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl, and $R^{16}$ represents hydrogen, halogen, $C_{1-6}$ alkyl, $C_{1-6}$ alkoxy, aryl, halo-aryl, aryloxy, aryl($C_{1-6}$)alkyl, aryl($C_{1-6}$) alkoxy or heteroaryl.

11. A compound selected from:

3-[4-(E)-(2-phenylethenyl)-1,2,3,6-tetrahydropyridin-1-yl] methylfuro[2,3-b]pyridine;

3-[4-(4-chlorophenyl)-1,2,3,6-tetrahydropyridin-1-yl] methylfuro[2,3-b]pyridine;

3-[4-(4-chlorophenyl)piperazin-1-yl]methylfuro[2,3-b] pyridine;

and salts and prodrugs thereof.

12. A pharmaceutical composition comprising a compound of formula I as defined in claim 1, or a pharmaceutically acceptable salt thereof or a prodrug thereof, in association with a pharmaceutically acceptable carrier.

13. A method for the treatment and/or prevention of disorders of the dopamine system, which comprises administering to a patient in need of such treatment an effective amount of a compound of formula I as defined in claim 1, or a pharmaceutically acceptable salt thereof or a prodrug thereof.

* * * * *